United States Patent [19]

Angelico et al.

[11] Patent Number: 4,917,898

[45] Date of Patent: Apr. 17, 1990

[54] PHARMACEUTICAL COMPOSITIONS FOR THE PROPHYLAXIS AND THERAPY OF CALCULOSIS OF BILIARY TRACT AND OF BILIARY DYSPEPSIA

[75] Inventors: Mario Angelico; Simos Contos, both of Florence, Italy

[73] Assignee: Pharmaricherche Di Allesandra Tonozzi e C. s.a.s., Milan, Italy

[21] Appl. No.: 200,945

[22] Filed: Jun. 1, 1988

[30] Foreign Application Priority Data

Jun. 3, 1987 [IT] Italy .............................. 20771 A/87

[51] Int. Cl.4 ................................................ A61K 9/48
[52] U.S. Cl. ..................................... 424/452; 424/106
[58] Field of Search ........................ 424/106, 486, 452

[56] References Cited

U.S. PATENT DOCUMENTS 4,263,272  4/1981  Frigerio .............................. 424/486

Primary Examiner—Ellis P. Robinson
Assistant Examiner—Leon R. Horne
Attorney, Agent, or Firm—Walter H Schneider

[57] ABSTRACT

Pharmaceutical compositions for the prophylaxis and therapy of biliary tract calculosis and of biliary dyspepsia, containing as the active principle taurohyodeoxycholic acid, are herein described.

4 Claims, No Drawings

PHARMACEUTICAL COMPOSITIONS FOR THE PROPHYLAXIS AND THERAPY OF CALCULOSIS OF BILIARY TRACT AND OF BILIARY DYSPEPSIA

The present invention relates to pharmaceutical compositions for the prophylaxis and the therapy of calculosis of biliary tract and for the treatment of biliary dyspepsia, containing as the active principle taurohyodeoxycholic acid, a natural biliary acid which up to now was not used in therapy.

Other biliary acids have been used for a long time as medicaments for the treatment of cholesterol biliary calculosis and of biliary dyspepsia, particularly ursodeoxycholic acid (UDCA) and the tauroconjugate thereof (TUDCA).

Taurohyodeoxycholic acid (THDCA), or 3 $\alpha$,6 $\alpha$-dihydroxy-5 $\beta$-cholanoyl-2-amino-ethyl-sulfonic acid, which is present as a minor component in pig bile (Biochem. J. 56.38–39, 1954), forms in intestine, following 7-alpha dehydroxylation of a primary biliary acid of the pig, i.e. hyodeoxycholic acid (HDCA) and subsequent hepatic conjugation with taurine.

THDCA, like the other natural dihydroxylated biliary acids, has the hydroxy group at the 3-alpha position, but it differs from said acids for the steric position of the second hydroxy group, which is at the 6-alpha position, instead of the 7-alpha (as in chenodeoxycholic acid), 7-beta (as in ursodeoxycholic acid) or 12-alpha (as in deoxycholic acid, DCA).

The presence of the hydroxy group at the 6-alpha position gives to THDCA remarkable chemico-physical properties, such as a retention time in reversed phase HPLC shorter than that of common biliary acids, said property being closely related to critic micell concentration (CMC) and to the ability to solubilize cholesterol. Furthermore, as another consequence of the presence of 6-alpha hydroxyl, THDCA is highly hydrophilic and has poor detergent power.

Unconjugated hyodeoxycholic acid has not been used in therapy up to now, even though two clinical works have already been published:

The first one is by Thistle and Schoenfield: HDCA in purified form at the dosage of 1 g/die was administered for 4 months to 5 calculotic subjects. The patients showed no side-effects nor changes in lipid secretion in bile, with the exception of a mild increase in lecithin/cholesterol molar ratio. An important result from this study is that the authors found in bile a very low percentage in HDCA (3% only) as if the latter was metabolized or eliminated by extrabiliary route. They could not give a satisfactory explanation of this phenomenon, but they admitted not to have an analytical method which could distinguish HDCA from the other dihydroxylated biliary acids or from the metabolites thereof.

In the second study (J. Lipid Res. 24,6 04, 1983) the authors administered 500 mg of HDCA to 5 patients having an external biliary fistula, and controlled biliary secretion and fecal and urinary secretions of the compounds and the metabolites thereof, using a radioactive labelled dose. This study proved the following:

(1) intestinal absorption of HDCA (administered through one gelatin capsule) is very efficient, as proved by fecal excretion of only a small radioactive fraction, during the 5 days following the administration;

(2) HDCA seems not to be metabolized by intestinal flora and, more particularly, as already stated above, it is not transformed into lithocholate;

(3) a remarkable aliquot of the administered HDCA (11.5% to 31%) is secreted in the bile in form of two metabolites, respectively identified as the glyco-conjugated derivative (GHDCA) and the 3-alpha-beta-D-glucuronyl-The latter glucurono-conjugated derivative is quite difficult to isolate and identify, and the results are not always satisfactory. On the other hand, the authors gave no evidences based on mass spectrometry of the compounds isolated from bile.

(4) A considerable amount of radioactivity administered in form of HDCA is excreted in the urines, apparently in form of glucuronyl-HDCA.

Glucurono-conjugation, making HDCA extremely hydrophilic, seems to be directly responsible for the high renal excretion, which is an unusual fact for a biliary salt which, by definition, should be concentrated in enterohepatic circulation. On the basis of such observation, Hofmann (J. Control Release 2, 3, 1985) defined unconjugated HDCA a "non enterohepatic" biliary acid. Such a definition, which however requires further confirmations in man in case of HDCA itself, does not apply to THDCA, since it seems to be unlikely, if not impossible, that the latter could be glucurono-conjugated: in fact, glucuronation consists in the conjugation of a biliary salt with glucuronic acid, and it takes place by the formation of an ester bond between the carboxy group of the side chain of the biliary salt and the hydroxy group at the 1-position of glucuronic acid. It is evident that said bond can be formed only for those biliary salts having a carboxy group in the side chain (i.e. the free and the glyco-conjugated forms), whereas it cannot be formed in those biliary salts having a sulfonic group in the side chain (i.e. the tauro-conjugated forms). Glucurono-conjugation can also take place by formation of an ester bond between the hydroxy group at the 3-position and glucuronic acid: also in this case, it seems to be limited to unconjugated biliary salts and, among these, mainly to the most hydrophobic ones. In other words, both ways of biliary salts glucuronation are able to detoxify compounds having a high detergent power and a high membrane-injuring potential, thus favouring the renal elimination thereof. Due to stereochemical or metabolic reasons, glucurono-conjugation does not affect tauroconjugated biliary salts, particularly the more hydrophilic ones, such as THDCA. For all the above reasons THDCA appears to behave as a physiologic biliary salt and effectively concentrate, in particular, in enterohepatic circulation. The validity of the invention, however, is not bound to the verification of the above hypothesis.

It has now been found that THDCA can modify the physical state of bile and affect cholesterol calculosis thanks to its ability to determine in bile a liquid-crystalline phase able to carry and solubilize cholesterol. With respect to the other drugs that are presently used, i.e. ursodeoxylic acid and tauroursodeoxylic acid, THDCA offers the following advantages:

(1) A low or absent hepatic metabolization.

(2) A low or absent intestinal metabolization in man that, unlike other animals, does not have an intestinal flora able to modify the hydroxy group at 6 $\alpha$.

(3) A lack of formation of lithocholic acid, a toxic biliary acid (Gastroenterol. 20, 112525, 1976) able to cause hepatic damages both of necrotic-degenerative and of cholestatic kind.

With respect to the unconjugated compound, THDCA is endowed with advantages bound to its solubility and ionization characteristics, to the absence of metabolization, to the ability to exert its physiologic action in enterohepatic circulation, to the absence of glucurono-conjugation and of renal excretion. As a matter of fact, the conjugation with taurine, thanks to the very low dissociation pka of taurine sulfonic group (lower than 1) makes THDCA soluble at all pH values. On the contrary, the unconjugated compound (and most likely the glyco-conjugated compound also) is insoluble at relatively acid pH values, like the values that are normally present in the duodenal lumen. Therefore, the compound unconjugated with taurine can precipitate and lose its effectiveness. Some preliminary data suggest the existence of remarkable differences in the solubility of THDCA and of the corresponding unconjugated compound (HDCA) or glyco-conjugated (GHDCA) that are not bound to variations of the pH values, but are a function of temperature.

The critical micell temperature (CMT), (or clarification point of a biliary salt solution, or Krafft point) seems to be higher than that of the common natural biliary salts: whereas the latter is close to 0° C., the ones of T-HDCA, HDCA and G-HDCA would be, for 10 mM concentrations, of 25°, 32° and 65° respectively. Therefore, at body temperature T-UDCA is likely to be the only compound that is completely soluble and able to fully exert its tensio-active detergent potential. On the contrary, HDCA and G-HDCA, if present at high concentrations, might be partially insoluble at body temperature, which might be responsible for the fact that in hamster G-HDCA intravenous infusion causes cholestasis (Gastroenterol, 65, 95, 1972).

Therefore, THDCA can be advantageously used as the active principle of pharmaceutical compositions for the treatment and prophylaxis of cholesterol cholelithiasis and in the symptomatic treatment of dyspepsia of biliary origin.

Posology, that depends on the kind of pathology to be treated and on the patient's conditions (weight, sex, age), will on the whole range from:

1. 3 to 8 mg/kg of body weight for the prophylaxis of biliary calculosis and for the therapy of biliary dyspepsia;

2. 5 to 15 mg/kg for litholytic therapy.

The daily dose of THDCA may be divided into two or three daily administrations, or in a unit dose to be taken in the evening. The administration may be carried out by means of gastro-resistant capsules, sustained release capsules, or tablets, each one containing from a minimum of 50 mg to a maximum of 400 mg of active principle.

The duration of the treatment may vary, according to indications, from a few weeks to several years.

The pharmaceutical compositions according to the present invention are prepared with conventional techniques and excipients, such as the ones described in "Remington's Pharmaceutical Sciences Handbook" Hack Pub. Co., New York, USA.

Taurohyodeoxycholic acid can be prepared by reaction of hyodeoxycholic acid with taurine, according to known methods.

The mechanism of action of taurohyodeoxycholic acid, to the verification of which, however, the validity of the invention is not bound, seems to be connected with the ability to modify the physical condition of bile, so that cholesterol, instead of being solubilized in the core of mixed micelles, is "dispersed" in liquid-crystalline lamellae rich in lecithin. This mechanism is virtually equal to monohydrate cholesterol dispersion that takes place in biologic membranes. This kind of change in the physical condition of bile can be obtained: (a) by increasing the biliary secretion of lecithin, in relation to the excretion of biliary salts; (b) by increasing the percentage of "hydrophilic" biliary salts; (c) by combining the two mechanisms.

We claim:

1. Pharmaceutical composition for the prevention and therapy of calculosis of the biliary tract and of biliary dyspepsia, containing as the active principle taurohyodeoxycholic acid in admixture with suitable carriers or excipients.

2. Composition according to claim 1 in the form of gastroresistant capsules, sustained release capsules, tablets.

3. Composition according to claim 1, containing between 50 and 400 mg of taurohyodeoxycholic acid for unit dose.

4. A method of treating a patient for the prevention and therapy of calculosis of the biliary tract and of biliary dyspepsia which comprises the administration of an effective amount of a composition according to claim 1.

* * * * *

UNITED STATES PATENT AND TRADEMARK OFFICE
CERTIFICATE OF CORRECTION

PATENT NO. : 4,917,898
DATED : April 17, 1990
INVENTOR(S) : Mario Angelico; Simos Contos It is certified that error appears in the above-identified patent and that said Letters Patent is hereby corrected as shown below:

On the Title page, the name of the Assignee "Pharmaricherche Di Allesandra Tonozzi e C. s.a.s" should read ---Pharmaricerche di Alessandra Tonozzi e C. s.a.s.---.

Signed and Sealed this

Twenty-seventh Day of August, 1991

Attest:

HARRY F. MANBECK, JR.

Attesting Officer

Commissioner of Patents and Trademarks